(12) United States Patent
Sauer et al.

(10) Patent No.: US 7,791,342 B2
(45) Date of Patent: Sep. 7, 2010

(54) CANCELLATION OF RINGING ARTIFACTS AND FAR FIELD INTERFERENCE IN NUCLEAR QUADRUPOLE RESONANCE

(76) Inventors: Karen L. Sauer, 4227 Berritt St., Fairfax, VA (US) 22030; Christopher A. Klug, 6301 Nicholson St., Falls Church, VA (US) 22044; Michael L. Buess, 4337 Taney Ave. #304, Alexandria, VA (US) 22304; Joel B. Miller, 3003 Crest Ave., Cheverly, MD (US) 20785

( * ) Notice: Subject to any disclaimer, the term of this patent is extended or adjusted under 35 U.S.C. 154(b) by 83 days.

(21) Appl. No.: 12/153,317

(22) Filed: May 16, 2008

(65) Prior Publication Data
US 2009/0027049 A1    Jan. 29, 2009

Related U.S. Application Data

(60) Provisional application No. 60/924,515, filed on May 18, 2007.

(51) Int. Cl.
*G01V 3/00* (2006.01)
(52) U.S. Cl. .................................................. 324/309
(58) Field of Classification Search ......... 324/300–322; 600/410–435
See application file for complete search history.

(56) References Cited
U.S. PATENT DOCUMENTS

| | | | |
|---|---|---|---|
| 5,206,592 A | 4/1993 | Buess et al. | |
| 5,233,300 A | 8/1993 | Buess et al. | |
| 5,365,171 A | 11/1994 | Buess et al. | |
| 5,608,321 A * | 3/1997 | Garroway et al. | 324/307 |
| 6,392,408 B1 | 5/2002 | Barrall et al. | |
| 6,566,873 B1 * | 5/2003 | Smith et al. | 324/300 |
| 7,109,705 B2 * | 9/2006 | Smith et al. | 324/300 |
| 7,292,033 B2 * | 11/2007 | Pusiol | 324/307 |

FOREIGN PATENT DOCUMENTS

| | | |
|---|---|---|
| WO | 93/11441 | 6/1993 |
| WO | 96/26453 | 8/1996 |

* cited by examiner

*Primary Examiner*—Brij B Shrivastav
*Assistant Examiner*—Dixomara Vargas

(57) ABSTRACT

A device for detecting a class of target species containing quadrupolar nuclei in a specimen by nuclear quadrupole resonance, comprising a pulse generator for generating a three-pulse-composite-pulse to refocus signals that were excited by another pulse, an irradiator for irradiating a specimen with the three-pulse-composite-pulse, a detector for detecting an NQR signal in response to irradiating the specimen, a coupler for transmitting the three-pulse-composite-pulse to the irradiating means, and a transformer for converting the free induction decay signal into a frequency domain signal. A method for detecting a class of target species containing quadrupolar nuclei in a specimen by nuclear quadrupole resonance, comprising generating a three-pulse-composite-pulse, irradiating said specimen with said three-pulse-composite-pulse, detecting an NQR signal in response to irradiating said specimen and converting said free induction decay signal into a frequency domain signal.

21 Claims, 2 Drawing Sheets

CANCELLATION OF RINGING ARTIFACTS AND FAR FIELD INTERFERENCE IN NUCLEAR QUADRUPOLE RESONANCE

CROSS-REFERENCE TO RELATED APPLICATIONS

This application claims the benefit of priority to U.S. provisional patent application Ser. No. 60/924,515, filed on May 18, 2007, entitled "Cancellation of Ringing Artifacts and Far Field Interference in Nuclear Quadrupole Resonance," which is incorporated by reference in its entirety.

BACKGROUND OF THE INVENTION (1) Field of the Invention

The present invention relates to the field of NQR detection and more specifically to apparatus and methods for improving the echo signal of NQR detection.

(2) Description of Related Art Including Information Disclosed Under 37 C.F.R. 1.97 and 1.98

Terrorist use of high explosives against people in aircraft and buildings has unfortunately become a fact of life. To date there are no commercial explosives detection systems which can reliably detect threat quantities of military explosive against a background of more benign materials. The essentially free flow of contraband narcotics in this country, arguably a less dramatic problem, has greater consequences within the US. There are, likewise, no good ways to check for narcotics in a rapid, accurate and noninvasive fashion.

A major problem with NQR detection is that the radio-frequency (RF) pulses used to generate NQR signals can also generate from benign material non-NQR signals which can be mistaken for or mask true NQR signals. Examples of such spurious signals include magnetoacoustic ringing in spring mechanisms and piezoelectric ringing in quartz crystals. Furthermore, in the unshielded environment of landmine detectors radio frequency interference (RFI) from radio stations can also hide or mimic a true NQR signal. Spurious ringing and RFI can be much stronger than an NQR signal and detecting explosives in the presence of such interference is a major challenge.

Many materials containing quadrupolar nuclei are most efficiently detected by NQR techniques that employ a multiple RF pulse sequence composed of a preparatory pulse followed by a train of equally spaced refocusing pulses. The preparatory pulse generates a bulk magnetization from the quadrupolar nuclei and that magnetization is refocused at regular intervals by the pulse train. The resulting NQR signal typically occurs as an echo centered midway between each pair of refocusing pulses and the echoes are summed in order to improve the signal-to-noise ratio.

However, spurious signals such as acoustic ringing will also be amplified by such echo summation. Standard techniques for eliminating such ringing involve modulating the phases of the preparatory and/or refocusing pulses in a way that modulates the NQR signal differently than it modulates the ringing. For example, if one could invert the ringing after every other pulse but leave the NQR signal unchanged (this is difficult in practice) then a summation of all echoes would yield the full NQR signal and be free of ringing. Unfortunately, most of those schemes reduce the NQR signal or only partially reduce the ringing signal (or both).

The spin-locked spin-echo (SLSE) pulse sequence is well suited for detecting explosives like TNT and PETN which have a long NQR spin-lattice relaxation time ($T_1$). In that pulse sequence the time interval between the preparatory pulse and the first pulse in the pulse train is one-half the pulse separation in the train, although sometimes the preparatory pulse interval is varied slightly to compensate for finite pulse length, filter delays and other effects that shift the position of the observed echo. The signal-to-noise ratio obtained in each scan is significantly enhanced by summing the train of echoes generated by the pulse sequence.

Unfortunately, spurious ringing is coherent with the pulses and, as a result, is also enhanced by echo summation. Spurious ringing can be cancelled to some extent by repeating the SLSE sequence with an inverted preparatory pulse as taught by Smith (PCT WO 96/26453). That inverts the NQR signal but not the ringing and proper summation of the two scans will enhance the NQR signal and reduce the ringing.

However, in order to maximize the NQR signal the scans must be separated by intervals greater than $T_1$, which can be several seconds. During those waiting intervals the properties of the material that is ringing, and therefore the ringing itself, can change due to RF heating for example. This makes it impossible to cancel the ringing entirely. Because RFI is not coherent with the pulses a multiple scan detection is as likely to enhance RFI interference as to suppress it. To be successful, a cancellation scheme must work on time scales for which ringing and RFI are essentially constant.

Barrall (U.S. Pat. No. 6,392,408) discusses a modified SLSE pulse sequence which periodically inverts the NQR signal (but not the ringing) during the refocusing pulse train such that summing the echoes in a manner that retains the NQR signal also cancels the ringing. However, the inversions typically occur at intervals of hundreds of milliseconds and the nature of the ringing can change in those intervals making its cancellation incomplete. RFI can change between inversions even more than the ringing and, as a consequence, this method is not effective at cancelling RFI. Inversions are also imperfect and a substantial amount of NQR signal is usually lost.

It is well known in NMR (Bloom), and has been demonstrated in NQR (Smith, PCT WO 93/11441), that a sequence of RF pulses spaced unequally will create a host of echoes within the pulse intervals. What is discussed by Bloom, but not explicitly acknowledged by Smith, is that the total available signal within an interval is constant and spreading an intense echo at the center of an interval into myriads of subsidiary echoes does not per se improve the signal-to-noise ratio (SNR). In fact, such a procedure usually reduces the SNR since the signal is spread out through the large interval necessary for the observation of multiple echoes.

Another pulse sequence that is sometimes used for NQR explosives detection is called MLEV-16. Like the SLSE pulse sequence it consists of a preparatory pulse followed by a train of equally spaced refocusing pulses. In the standard form of the pulse sequence the preparatory pulse interval is also approximately one-half of the refocusing pulse interval. But the phases of the RF pulses in the MLEV-16 pulse sequence alternate in such a way that summing the echoes produces a net NQR signal but no net ringing.

Ringing cancels quite well in this pulse sequence because cancellation occurs within each 16-pulse cycle (on the order of tens, rather than hundreds or thousands, of milliseconds). Unfortunately, the net NQR signal for the MLEV-16 pulse sequence is approximately 50% smaller than that produced by a comparable SLSE pulse sequence. The SLSE and MLEV-16 pulse sequences each have two different pulse intervals (preparatory and refocusing) and the standard forms of both pulse sequences generate two types of echoes that occur at the center of each refocusing pulse interval. However, the echoes produced by MLEV-16 interfere more destructively than those produced by SLSE.

BRIEF SUMMARY OF THE INVENTION

In one aspect, the present invention relates to a device for detecting a class of target species containing quadrupolar nuclei in a specimen by nuclear quadrupole resonance. The device includes: (a) a pulse generator for generating a three-pulse-composite-pulse; (b) an irradiator for irradiating a specimen with the three-pulse-composite-pulse; (c) a detector for detecting an free induction decay NQR signal having a true signal component, a ringing signal component and a radio frequency interference component in response to irradiating the specimen; (d) a coupler for transmitting the three-pulse-composite-pulse to the irradiating means; and (e) a transformer for processing said detected free induction decay NQR signals to cancel the ringing signal component and convert the free induction decay signal into a frequency domain signal.

In another aspect, the present invention relates to a method for detecting a class of target species containing quadrupolar nuclei in a specimen by nuclear quadrupole resonance. The method includes the steps of: (a) generating a three-pulse-composite-pulse; (b) irradiating the specimen with said three-pulse-composite-pulse; (c) detecting a free induction decay NQR signal having a true signal component, a ringing signal component and a radio frequency interference component in response to irradiating said specimen; (d) processing said free induction decay NQR signal to cancel the ringing signal component, and (e) converting said free induction decay signal into a frequency domain signal. The method may be used to detect target species including explosives such as trinitrotoluene and narcotics such as cocaine hydrochloride.

DETAILED DESCRIPTION OF THE INVENTION

Figure 1:
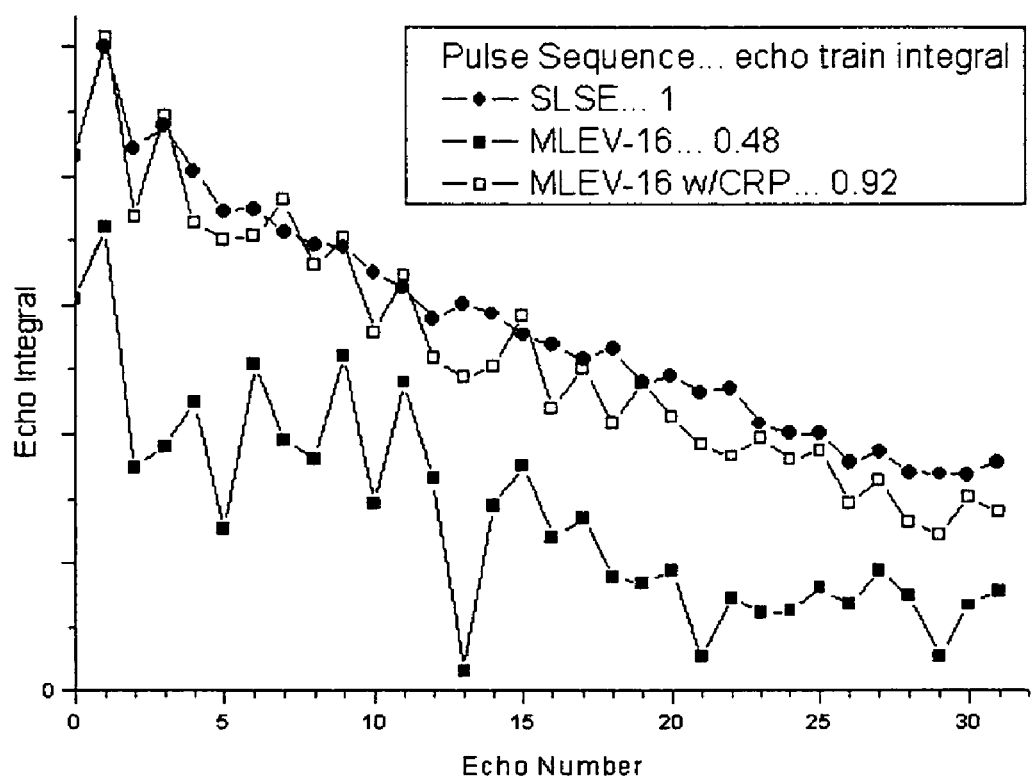
FIG. 1 is graph showing the comparison of the NQR response in glycine hemichloride at 834 kHz to SLSE and MLEV-16 with and without composite refocusing pulses (CRP). Refocusing pulse interval was 0.64 ms in each case.

It is disclosed here that under certain conditions the phase and position of the resulting echoes can be manipulated in a manner that allows the cancellation of both spurious ringing and RFI with a loss in SNR that is no greater than that which results from current methods that cancel ringing alone.

In an earlier disclosure (AA Means for Improving the Detection of Explosives and Narcotics by Time-Shifted Nuclear Quadrupole Resonance (NQR)@, 1995) we described a variation of the SLSE pulse sequence which splits the observed NQR echo by moving the two echo types in opposite directions away from the center of the refocusing pulse interval. This splitting is accomplished by retarding or advancing the pulse train with respect to the preparatory pulse. When the resulting echoes are shifted far enough apart to avoid interference their intensities are each one-half of the unsplit echo.

There is a recovery period following each high power (ca 1 kW) RF pulse during which the receiver is overloaded: only after the energy in the tuned RF probe has dissipated and the receiver recovered can the weak NQR signal be observed. Hence the echo in the second half of the pulse interval is much easier to observe than the echo in the first half. Since its intensity is one-half that of the unsplit echo the sum of all echoes in the second half of the pulse intervals will also be approximately one-half of the sum of unsplit echoes.

Furthermore, alternating the phases of the RF pulses in the SLSE pulse train between 0" and 180" will produce an echo train in which the observable echoes alternate in sign. Processing of such an echo train is accomplished by digitally inverting every other echo prior to summation and that will cancel RFI that is constant during each pair of echoes. Unfortunately, spurious ringing is coherent with the pulses and will not cancel with such a pulse sequence.

It is disclosed here that certain types of refocusing pulse favor the creation of one type of echo above the other. When only one type of echo is present there will be no destructive interference. In the case of the MLEV-16 pulse sequence destructive interference can be virtually eliminated by using the proper refocusing pulse and this allows for the cancellation of ringing with little or no loss in SNR. By splitting the echoes, RFI can be canceled with 50% reduction in SNR.

This invention provides a means for increasing the signal intensity and decreasing the effects of interference in the detection by nuclear quadrupole resonance (NQR) of nitrogenous or chlorine-containing explosives such as trinitrotoluene or narcotics such as cocaine hydrochloride (or, more generally, materials containing quadrupolar nuclei such as $^{14}N$, $^{35,37}Cl$, $^{39}K$, etc.), such as contained in landmines or carried in luggage, mail, small cargo or on a person. The utility of NQR detection of explosives and narcotics was previously taught in NRL work: U.S. Pat. No. 5,206,592 (27 Apr. 1993), U.S. Pat. No. 5,233,300 (3 Aug. 1993), U.S. Pat. No. 5,365,171 (15 Nov. 1994), and U.S. Pat. No. 5,608,321 (4 Mar. 1997), as well as other related NRL patent disclosures.

The method disclosed here is based on the fundamental understanding that multiple pulse sequences generate more than one type of NQR echo that interfere constructively or destructively to produce the net (observed) NQR signal. It is shown that certain composite refocusing pulses can mitigate the destructive interference of those echoes and thereby regain most of the NQR signal that is normally lost by pulse sequence modulation techniques that are effective at cancelling spurious ringing. Furthermore, a method is disclosed for temporally separating the echoes within each pulse interval which provides the opportunity to cancel RFI as well as ringing.

Herein it is disclosed that a particular composite pulse comprised of three single pulses with spin-flip angles of 240° and RF phases of 300°, 60° and 300° works well as a refocusing pulse. FIG. 1 compares the NQR response in glycine hemihydrochloride to the SLSE pulse sequence with its response to an MLEV-16 pulse sequence comprised of single pulses and one comprised of our 3-pulse composite pulses. The NQR frequencies, line widths and relaxation times of glycine hemihydrochloride are similar to those of TNT making it a reasonable compound on which to test pulse sequences designed for TNT detection. The integrals of the echo trains in MLEV-16 sequences with single and composite pulses are 50% and 90% as large, respectively, as that in the SLSE sequence which demonstrates the improvement in signal intensity provided by this composite pulse.

It is noted that other composite pulses might exist that perform even better in MLEV type pulse sequences.

When the MLEV-16 pulse train is retarded or advanced with respect to the preparatory pulse only one of the resulting echoes appears in each pulse interval. Odd numbered intervals contain only the earlier echo while even numbered intervals contain only the later echo. (Or vice versa, depending on whether the pulse train was retarded or advanced.) Once again, the later echoes are easier to observe because of receiver overload. However, when using our composite refocusing pulses, the observable echoes have the full intensity of the corresponding unsplit echo. Although half as many split echoes are observed in the MLEV-16 pulse sequence their combined intensity is still approximately one-half of that of the corresponding unsplit MLEV-16 echoes.

With the MLEV-16 pulse sequence ringing cancels among the odd-numbered and even-numbered pulse intervals separately. If every other echo signal is digitally inverted prior to summation spurious ringing will still be effectively eliminated. With the refocusing pulse intervals commonly used in explosives detection (less than 2 ms) RFI will change very little from one pulse interval to the next and will also cancel when processed in this manner. Therefore, an MLEV-16 pulse sequence using split-echoes will cancel both spurious ringing and RFI. However, if the pulse sequence uses standard (non-composite) refocusing pulses it will generate approximately 25% as much NQR signal as a comparable standard SLSE pulse sequence. (50% is lost merely by using MLEV-16 and 50% of the remainder is lost by splitting the echoes.)

When the three-pulse composite pulse discussed above is used to refocus the split (time-shifted) echoes in MLEV-16 an observable echo occurs in every pulse interval but the amplitude of every other echo is reduced and it is approximately 90° out of phase with the rest. After inverting every other echo and then summing all echoes it is found that the net NQR signal from glycine hemihydrochloride is 50% as intense as that obtained from a standard SLSE pulse sequence. As with the standard MLEV-16 pulse sequence, the composite refocusing pulse improves the NQR signal intensity by a factor of two.

Certain composite refocusing pulses, such as the one described here, create more of one type of echo than the other and thereby reduce destructive interference between the two types of echoes. This can be used to tailor pulse sequences that cancel magnetoacoustic and piezoelectric ringing but still create a detectable amount of NQR signal. Splitting the echoes by retarding or advancing the pulse train with respect to the preparatory pulse allows the further cancellation of RFI with a 50% reduction in the NQR signal.

Figure 2:
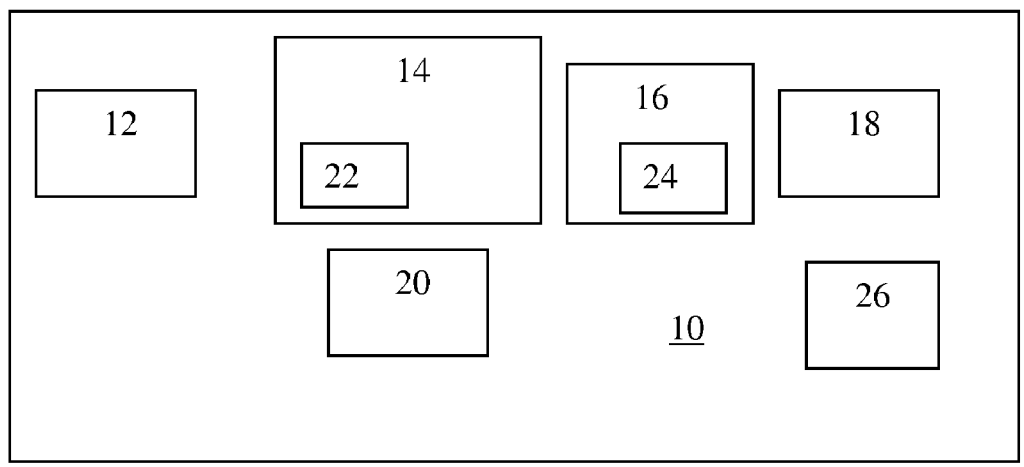
FIG. 2 is a schematic representation of an NQR system in accordance with the present invention.

An NQR system 10 suitable for carrying out the method of the present invention is shown schematically in FIG. 2. The NQR system 10 includes a pulse generator 12 for generating a three-pulse composite pulse which may be used to refocus signals that were excited by another pulse, an irradiator 14 for irradiating a specimen with the three-pulse composite pulse, a detector 16 for detecting a free induction decay NQR signal, a coupler 18 for transmitting the three-pulse composite pulse to the irradiating means and a transformer 20. Irradiator 14 may include a coil 22 and detector 16 may include a coil 24. NQR system 10 may also optionally include a component 26 for computing the width of a selected peak in a frequency domain signal.

Detected NQR signals may have a true signal component, a ringing signal component and a radio frequency interference component. Transformer 20 may process the free induction decay NQR signals from the detector to cancel the ringing signal and radio frequency interference components.

The three-pulse composite pulse may have a preselected frequency distribution. The preselected frequency distribution of the three-pulse composite pulse may optionally include an NQR peak of the target species, preferably the full width at half maximum of an NQR peak of the target species. There may be a pulse interval of about 500 to about 5000 microseconds, preferably from about 50 to about 2000 microseconds between each pulse of the composite pulse and each pulse may have duration of about 50 to about 500 microseconds. Each of the three single pulses of the composite pulse may have a spin-flip angle of 240 degrees and the three single pulses may have RF phases of 300, 60 and 300 degrees. The composite pulse may be preceded by a generated first pulse which may be selected from the group consisting of a single pulse, a composite pulse, a phase-modulated pulse, an amplitude-modulated pulse and a phase- and amplitude-modulated pulse, wherein the first pulse creates an NQR signal.

The system may apply further excitation to the sample subsequent to the three pulse composite pulse and detect an NQR response signal therefrom. The three pulse composite pulse may be used to refocus a split or time-shifted echo in MLEV-16. The three pulse composite pulse may produce an observable echo which occurs in every pulse interval but the amplitude of every other echo is reduced. The refocusing pulse may improve the NQR signal intensity by a factor of two as compared to a standard MLEV-16 pulse sequence.

The ringing signal may be canceled by digitally inverting every other detected free induction decay NQR signal and subsequently summing all of the inverted and non-inverted detected free induction decay NQR signals. The NQR signal may also be processed to identify a true signal component and to cancel a RFI signal. The set of RF pulse sequences of the composite pulse may have a predetermined frequency near to a $^{14}N$, $^{35}Cl$ or $^{37}Cl$ NQR frequency of the substance to be detected. The substance to be detected may be, for example, an explosive including a $^{14}N$ nucleus.

The above description is that of a preferred embodiment of the invention. Various modifications and variations are possible in light of the above teachings. It is therefore to be understood that, within the scope of the appended claims, the invention may be practiced otherwise than as specifically described. Any reference to claim elements in the singular, e.g., using the articles "a," "an," "the," or "said" is not construed as limiting the element to the singular.

What is claimed is:

1. A device for detecting a class of target species containing quadrupolar nuclei in a specimen by nuclear quadrupole resonance, comprising:
    (a) a pulse generator for generating a three-pulse-composite-pulse;
    (b) an irradiator for irradiating a specimen with the three-pulse-composite-pulse;
    (c) a detector for detecting free induction decay NQR signal having a true signal component, a ringing signal component and a radio frequency interference component in response to irradiating the specimen;
    (d) a coupler for transmitting the three-pulse-composite-pulse to the irradiating means; and
    (e) a transformer for processing said detected free induction decay NQR signals to cancel the ringing signal component and convert the free induction decay signal into a frequency domain signal.

2. The device of claim 1, wherein the irradiator and the detector comprise a coil.

3. The device of claim 2, wherein said irradiator comprises a first coil and said detector comprises a second coil and wherein the three-pulse-composite-pulse refocuses signals that were excited by another pulse.

4. The device of claim 1, wherein said target species are selected from the group consisting of narcotics and explosives.

5. The device of claim 4, wherein said target species are selected from the group consisting of cocaine hydrochloride and trinitrotoluene.

6. The device of claim 1, further comprising a component for computing the width of a selected peak in said frequency domain signal.

7. The device of claim 1, wherein said three-pulse-composite-pulse has a preselected frequency distribution.

8. The device of claim 7, wherein said preselected frequency distribution includes an NQR peak of said target species.

9. The device of claim 8, wherein said preselected frequency distribution includes the full width at half maximum of an NQR peak of said target species.

10. A device as claimed in claim 1, wherein said transformer digitally inverts every other detected echo of the free induction decay NQR signal and subsequently sums all of the inverted and non-inverted detected echoes of the free induction decay NQR signals.

11. A device as claimed in claim 10, wherein there is a pulse interval of about 500 to about 5000 microseconds between each pulse of said composite pulse and each pulse has a duration of about 50 to about 500 microseconds.

12. A device as claimed in claim 11, wherein the pulse interval is from about 500 to about 2000 microseconds.

13. A device as claimed in claim 11, wherein each of the three single pulses of the composite pulse has a spin-flip angle of 240 degrees and the three single pulses have RF phases of 300, 60 and 300 degrees.

14. A method for detecting a class of target species containing quadrupolar nuclei in a specimen by nuclear quadrupole resonance, comprising:
   (a) generating a three-pulse-composite-pulse;
   (b) irradiating said specimen with said three-pulse-composite-pulse;
   (c) detecting a free induction decay NQR signal having a true signal component, a ringing signal component and a radio frequency interference component in response to irradiating said specimen;
   (d) processing said free induction decay NQR signal to cancel the ringing signal component, and
   (e) converting said free induction decay signal into a frequency domain signal.

15. The method of claim 14, wherein said target species are selected from the group consisting of narcotics and explosives.

16. The method of claim 15, wherein said target species are selected from the group consisting of cocaine hydrochloride and trinitrotoluene.

17. A method as claimed in claim 14, wherein said detected free induction decay NQR signal is processed by digitally inverting every other detected echo of the free induction decay NQR signal and subsequently summing all of the detected echoes of the free induction decay NQR signals.

18. A method as claimed in claim 17, wherein there is a pulse interval of about 500 to about 5000 microseconds between each pulse of said composite pulse and each pulse has a duration of about 50 to about 500 microseconds.

19. A method as claimed in claim 18, wherein the pulse interval is from about 500 to about 2000 microseconds.

20. A method as claimed in claim 18, wherein each of the three single pulses of the composite pulse has a spin-flip angle of 240 degrees and the three single pulses have RF phases of 300, 60 and 300 degrees.

21. A method as claimed in claim 20, wherein the three pulse composite pulse refocuses split or time-shifted echoes in an MLEV-16 pulse sequence.

* * * * *